United States Patent Office

Plant Pat. 2,128
Patented Jan. 30, 1962

2,128
ROSE PLANT

Eugene S. Boerner, Newark, N.Y., assignor to Jackson & Perkins Company, Newark, N.Y., a corporation of New York Filed Mar. 17, 1961, Ser. No. 96,630
1 Claim. (Cl. 47—61)

The present invention relates to a new and distinct variety of rose plant of the hybrid tea class, which was originated by me by crossing the variety "Princess White" (Plant Patent No. 1,540) with an unnamed and unpatented white hybrid tea seedling.

The primary objective of this breeding was to produce a new rose variety of the hybrid tea class and in which the flowers have stiff petals and better keeping qualities for cut flower use as compared with those of the parent variety "Princess White." This objective was fully achieved, along with other desirable improvements, as evidenced by the following unique combination of outstanding characteristics which distinguish it from its parents, as well as from all other varieties of which I am aware:

(1) Very fine, dark green foliage;
(2) Long individual flower stems;
(3) Prolific flower production;
(4) A medium flower size of hybrid tea form;
(5) Firm and long-lasting flower petals in both the bud and open flower stages;
(6) A distinctive Pure White general color tonality of the flowers in the open flower stage; and
(7) Long lasting qualities of the flowers both on the plant and as cut flowers.

Asexual reproduction of my new variety by budding, as performed at Newark, New York, and also at Pleasanton, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
*Seed parent.*—"Princess White."
*Pollen parent.*—An unnamed white hybrid tea seedling.

Classification:
*Botanic.*—Hybrid tea.
*Commercial.*—Hybrid tea.

*Flower*

(Observations made from specimens grown in a greenhouse at Newark, New York, in the early morning during the middle part of the month of September.)

Blooming habit: Recurrent—continuous, and with a great production of bloom.

Bud:
*Size.*—Medium.
*Form.*—Ovoid; is not affected by wet or hot weather.
*Color.*—When sepals first divide—Clear Dull Green-Yellow, Plate 17. When petals begin to unfurl—White, Plate 53, lightly overcast with Deep Sea-Foam Green, Plate 31. When half-blown: inside of petals—White, Plate 53, with base of petals lightly overcast with Pale Glass Green, Plate 31; reverse of petals—White, Plate 53, with base of petals lightly overcast with Pale Dull Green-Yellow, Plate 17.
*Sepals.*—Slightly branched; curl back when petals begin to unfurl. Color: inside—Biscay Green, Plate 17; outside—Courge Green, Plate 17, lightly overcast at the base with Acajou Red, Plate 13.
*Calyx.*—Color—Biscay Green, Plate 17. Shape—apple. Size—broad. Aspect—smooth. Odor when rubbed—none.
*Peduncle.* — Length — medium. Aspect — rough. Strength—erect; heavy. Color—Biscay Green, Plate 17, lightly overcast with Acajou Red, Plate 13.
*Opening.*—Opens up well; is not affected by adverse weather conditions.

Bloom:
*Size.*—Large. Average size when fully expanded—4 inches.
*Borne.*—Singly.
*Stems.*—Long; strong.
*Form (when first open).*—High-centered. Permanence—retains its form to the end.
*Petalage.*—Double (full but open center). Number of petals under normal conditions—from 40 to 45.
*Color.*—Center of flower—White, Plate 53, with lower half of petals lightly overcast with Sea-Foam Yellow, Plate 31. Outer petals—White, Plate 53. Base of petals (aiglet)—Sea-Foam Green, Plate 31. Inside of petals—White, Plate 53. Reverse of petals—White, Plate 53. General tonality from a distance—White, Plate 53.
*Discoloration.*—General tonality at end of first day—White, Plate 53. Second day—White, Plate 53. Third day—White, Plate 53.

Petals:
*Texture.*—Leathery; firm; long-lasting in both bud and open stages; is not affected by wet or hot weather.
*Appearance.*—Inside—satiny. Outside—shiny.
*Form.*—Oval.
*Arrangement.*—Imbricated (regularly arranged shingle-like).
*Petaloids in center.*—Few; large.
*Persistence.*—Drop off cleanly.
*Fragrance.*—Moderate. Nature—tea (average hybrid tea scent).
*Lasting quality.*—On the plant—very long. As cut flower—very long.

*Genital organs*

Stamens, anthers: Medium size; many; regularly arranged around styles. Color—Antimony Yellow, Plate 15.
Stamens, filaments (threads): Medium length. Color—Ivory Yellow, Plate 30.
Pollen: Color—Light Buff, Plate 15.
Styles: Columnar; uneven length; medium length; thin.
Stigmas: Color—Light Ochraceous-Buff, Plate 15.
Ovaries: All enclosed in calyx.
Hips: None.
Seeds: None.

*Plant*

Form: Bush.
Growth: Vigorous; upright.
Foliage: Compound of 5–7 leaflets.
*Size.*—Large.
*Quantity.*—Abundant.
*Color.*—New foliage: upper side—Lettuce Green, Plate 5, with edge of leaf lightly overcast with Oxblood Red, Plate 1; under side—Oil Green, Plate 5, lightly overcast with Oxblood Red, Plate 1. Old foliage: upper side—Dark Cress Green, Plate 31; under side—Light Bice Green, Plate 17.

*Shape.*—Oval pointed.

*Texture.*—Upper side—leathery. Under side—smooth.

*Ribs and veins.*—Ordinary.

*Edge.*—Serrated (saw-toothed).

*Serration.*—Both double and single; small.

*Leaf stem.*—Color—Oil Green, Plate 5. Under side—prickly.

*Stipules.*—Medium length; bearded.

Wood:

*New Wood.*—Color—Light Elm Green, Plate 17. Bark—smooth.

*Old wood.*—Color — Varley's Green, Plate 18. Bark—smooth.

Thorns:

*Thorns.*—Quantity: on main stalks from base—ordinary; on laterals from stalk—ordinary. Form—narrow base; medium length; straight. Color (when young)—Carmine, Plate 1. Position—irregular.

*Prickles.*—Quantity: on main stalks—none; on laterals—none.

*Short needles.*—Quantity: on main stalks—none; on laterals—none.

I claim:

A new and distinct variety of rose plant of the hybrid tea class, substantially as herein shown and described, characterized particularly as to novelty by the unique combination of very fine, dark green foliage, long individual flower stems, prolific flower production, medium flower size, firm and long-lasting flower petals in both the bud and open flower stages, a distinctive Pure White general color tonality of the flowers in the open stage, and very long-lasting qualities of the flowers both on the plant and as cut flowers.

No references cited.

Jan. 30, 1962 E. S. BOERNER Plant Pat. 2,128
ROSE PLANT
Filed March 17, 1961
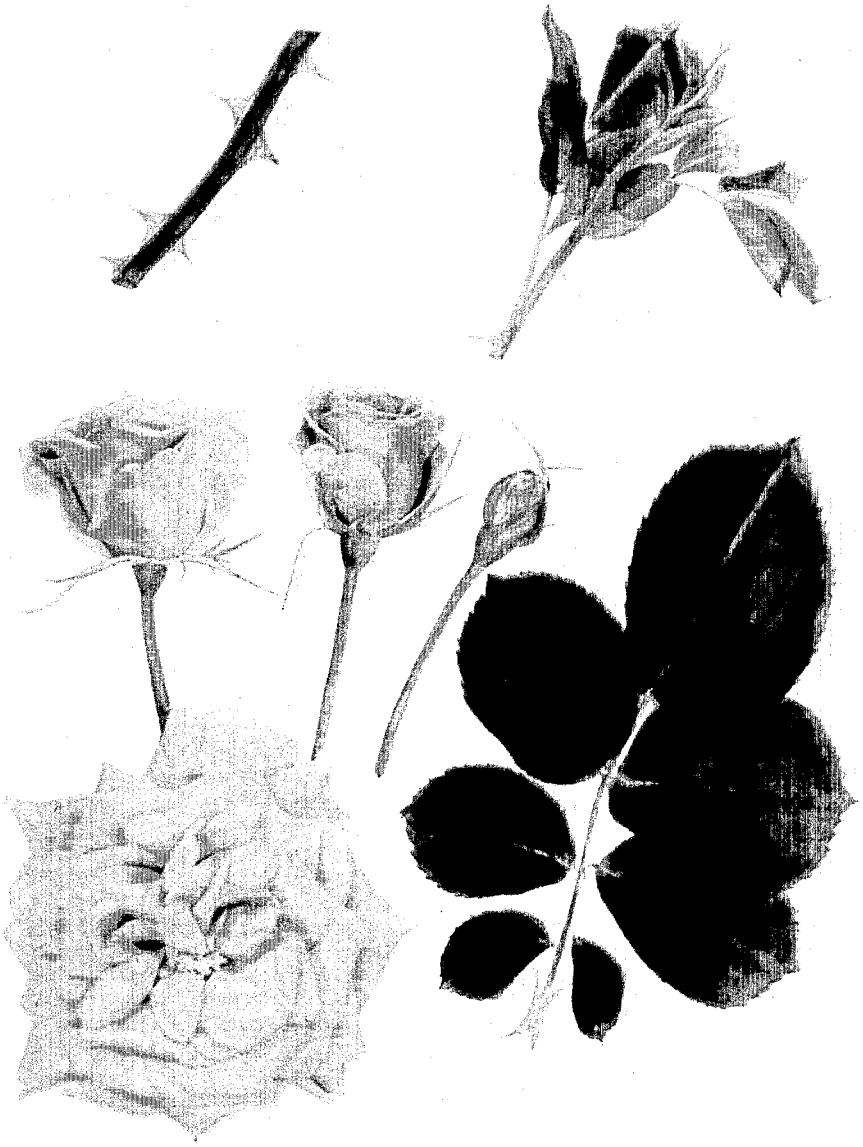
Inventor.
E. S. Boerner
By: Robb & Robb
Attorneys.

Jan. 30, 1962 E. S. BOERNER Plant Pat. 2,128
ROSE PLANT
Filed March 17, 1961
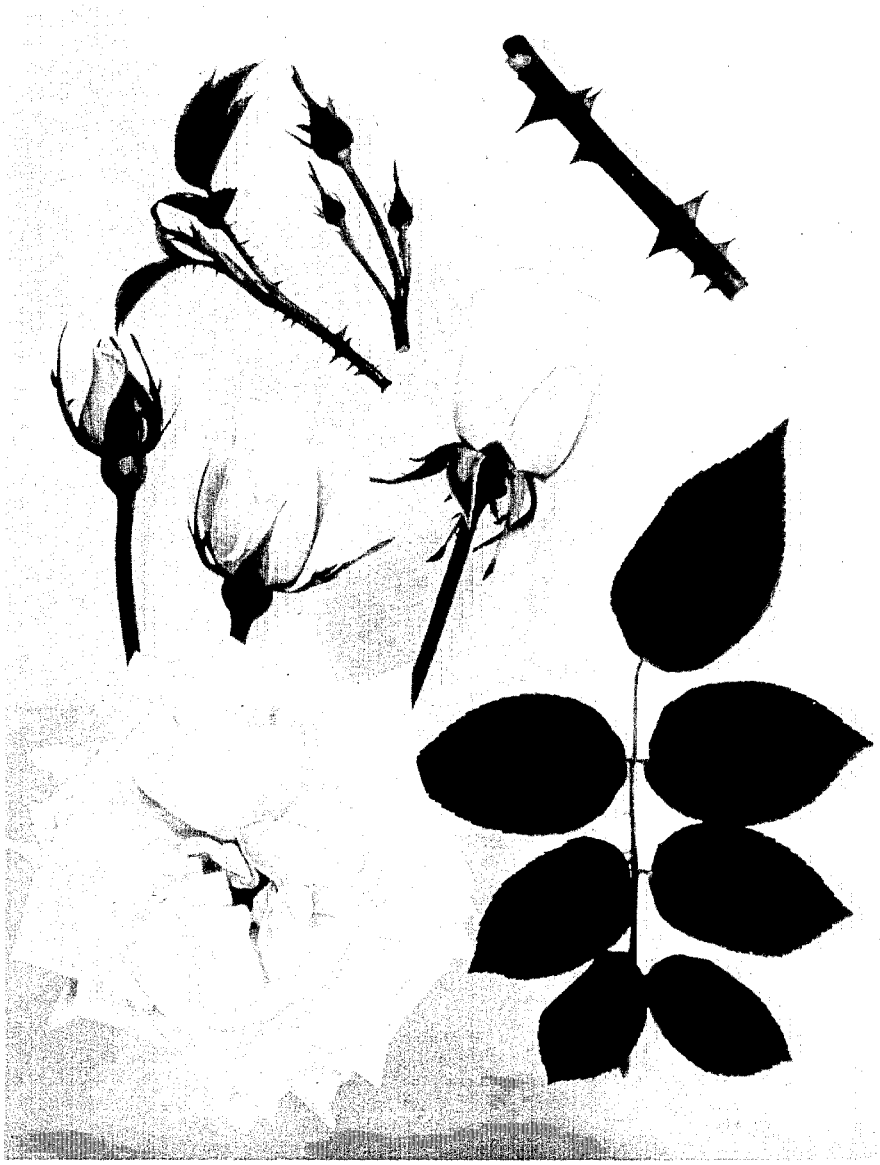
Inventor.
E. S. Boerner
By: Robb & Robb
Attorneys.

UNITED STATES PATENT OFFICE

Certificate of Correction

Plant Pat. No. 2,128 January 30, 1962

Eugene S. Boerner

It is hereby certified that error appears in the above numbered patent requiring correction.

The present sheet of drawing should be cancelled and the attached sheet substituted therefor, as part of the Letters Patent.

Signed and sealed this 15th day of May 1962.

[SEAL]

Attest:

ERNEST W. SWIDER,
*Attesting Officer.*

DAVID L. LADD,
*Commissioner of Patents.*